United States Patent [19]

Smith

[11] Patent Number: 4,862,891
[45] Date of Patent: Sep. 5, 1989

[54] DEVICE FOR SEQUENTIAL PERCUTANEOUS DILATION

[75] Inventor: Steven M. Smith, Salt Lake City, Utah

[73] Assignee: Canyon Medical Products, Salt Lake City, Utah

[21] Appl. No.: 167,716

[22] Filed: Mar. 14, 1988

[51] Int. Cl.$^4$ .............................................. A61M 29/00
[52] U.S. Cl. ..................................... 128/343; 604/104
[58] Field of Search ....................... 128/341, 343, 772; 604/104

[56] References Cited

U.S. PATENT DOCUMENTS

| | | | |
|---|---|---|---|
| 3,811,449 | 5/1974 | Graulee et al. | 128/343 |
| 4,449,532 | 5/1984 | Storz | 128/341 |
| 4,629,450 | 12/1986 | Suzuk et al. | 128/343 X |
| 4,686,984 | 8/1987 | Bonnet | 128/343 |

Primary Examiner—Dalton L. Truluck
Attorney, Agent, or Firm—Thorpe, North & Western

[57] ABSTRACT

A device for enabling sequential dilation of a percutaneous tissue opening to seccessively larger opening sizes. The device includes a first-elongated dilator element having a forward end, an intermediate dilator body and a tail section extending from shoulder structure at the junction of the intermediate body and tail section. At least one additional elongated tubular dilator is adapted for telescopic mounting over the first dilator element and includes a forward end, intermediate body, rearward end and blocking member. This dilator is tubular in construction and sized to fit snugly around the first dilator element in telescoping manner. The blocking member positioned at a rearward end of the dilator allows it to be seated in a forward-most position, in contact with the shoulder structure of the first dilator element. Additional dilators of successively larger diameters can be added to increase the extent of tissue dilation. Removal of the dilator device is accomplished by grasping the tail section and withdrawing the system from within a sheath or cannula emplaced to link a patient to an extracorporeal circulatory system.

10 Claims, 4 Drawing Sheets

DEVICE FOR SEQUENTIAL PERCUTANEOUS DILATION

BACKGROUND OF THE INVENTION

1. Field of the Invention

This invention relates to devices for enabling sequential percutaneous dilation of a tissue opening to permit subsequent insertion of a large cannula. More particularly, the present invention pertains to a sequential dilator system that utilizes a series of telescoping dilators of gradually increasing size.

2. Prior Art

Numerous procedures exist for obtaining percutaneous access to the vascular system. For example, percutaneous vascular catheterization for small diameter cannulae has been accomplished by use of a thin wall entry needle in accordance with the Seldinger technique. *Acta Radiologica*, 38:368–376, 1953. This involves passing a guide wire through the lumen of the entry of the needle for proper positioning within the vessel. The needle is then withdrawn and a small catheter is inserted over the guide wire and twisted through the tissue opening with minimal trauma. The guide wire is then removed and the cannula is placed in operation.

Although similar placement of small diameter cannulae is routinely done thousands of times each day in hospitals, placement of larger cannulae has been limited. For example, cannulae needed for delivery of up to six liters of blood flow per minute requires a large percutaneous opening for cannulae of up to 28 French in size. In the past, a surgical cut-down procedure requiring the presence of a surgeon has been necesary.

More recently, techniques have been developed which enable gradual dilation of a small percutaneous opening to the required large size. Tapered dilators have been developed which are small at the tip and which increase in diameter to a desired dilation radius. Such tapered design, however, is not well suited for telescopic emplacement of the cannulae, whose diameter is generally uniform to provide better flow dynamics. Therefore, introduction of large cannulae by dilators with extreme tapered configuration has not been practical.

Other techniques have been developed in prototype stage which provide gradual dilation without cut-down. One such method utilizes a device manufactured by Adam Spence Corporation of Wall, New Jersey, as part of procedure for removing kidney stones. This device comprises a series of telescoping tubes, each tube having a uniform diameter slightly larger than the tube diameter which is inserted within its bore. These tubes may be slid in both directions in telescoping relationship and pose the problem of smaller tube ends sliding within the bore of a larger tube, thereby losing grasp of the tube end for withdrawal. In essence each smaller tube has substantially greater length than the larger tubes, and basically operates as a guide wire for the next tube mounted thereon. This pattern of decreasing the length of the tube with increasing diameter requires the physician to guess as to the desired positioning location of each telescoping section. Obviously, there is no guarantee that correct positioning will remain during patient use even if the correct position is initially applied. This unpredictable character not only increases risk to the patient, but also adds difficulty to the attending medical staff. The device is not well-suited for use within the circulatory system.

It would be desirable to have a more rapid and simplistic approach to patient cannulation which does not depend on the exercise of extreme care by medical staff for proper emplacement of the catheter. Such procedures are particularly needed for the growing number of frequent emergency extracorporeal cardio-pulmonary bypass operations. Furthermore, a true percutaneous method of cannulation would eliminate the need for surgical cut-down often practiced with respect to cannulation of the femoral vein and artery, thereby allowing a broader range of hospital based physicians to implement the procedure.

OBJECTS AND SUMMARY OF THE INVENTION

It is an object of the present invention to provide an improved system for sequential dilation of a tissue opening which avoids the need for surgical cut-down and increases the simplicity and safety of cannula insertion.

It is a further object of the present invention to provide a sequential dilation device which permits use of successive dilator elements which enlarge the tissue opening to the extent needed for insertion of a cannula or catheter, while minimizing blood loss and without complication due to tearing of tissues.

It is a further object of this invention to provide a sequential dilation device useful as part of procedures requiring access to the circulatory system such as a femoral bypass and which simplify emplacement of a percutaneous bypass cannula system having a high flow rate with acceptable levels of hemodynamics.

A still further object of the present invention is to provide such a dilator system which can be easily removed just prior to emplacement of a desired catheter or cannulae to be used for accessing the circulatory system.

These and other objects are realized in a device which comprises a first elongated dilator element having a forward end, an intermediate dilator body of uniform diameter and a tail section of smaller diameter. The intermediate body includes rearwardly disposed shoulder structure at the point of juncture with the smaller diameter of the tail section. At least one additional elongated, tubular dilator is telescopically mounted around the first dilator element. Such additional dilators have a tubular wall and tubular opening slightly larger in diameter than the diameter of the first dilator element or any intermediate dilator elements. Each dilator has a forward end, an intermediate body and a rearward end with rearward blocking means. This rearward blocking means limits forward positioning of the additional dilators such that they cannot extend beyond the forward end of the first dilator element. Such blocking means restrict forward movement by butting against the shoulder structure of the first element. The present device enables use of multiple dilators which can enlarge a percutaneous access opening to as much as 28 French. This device permits atraumatic expansion of tissues and vessel walls with minimal blood loss and usually eliminates the need of cut-down or similar surgical procedures. Implementation of this dilator system is easier, faster and safer than other prior art methods of cannulation.

Other objects and features of the present invention will be apparent to those skilled in the art, based upon the following detailed description and view of the accompanying drawings.

DETAILED DESCRIPTION OF THE INVENTION

Figure 10:
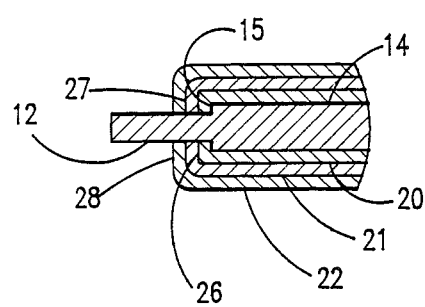
FIG. 10 discloses a cross sectional view of the device illustrated in FIG. 1 showing a direct view of item 15 and surrounding structure.
Figure 1:
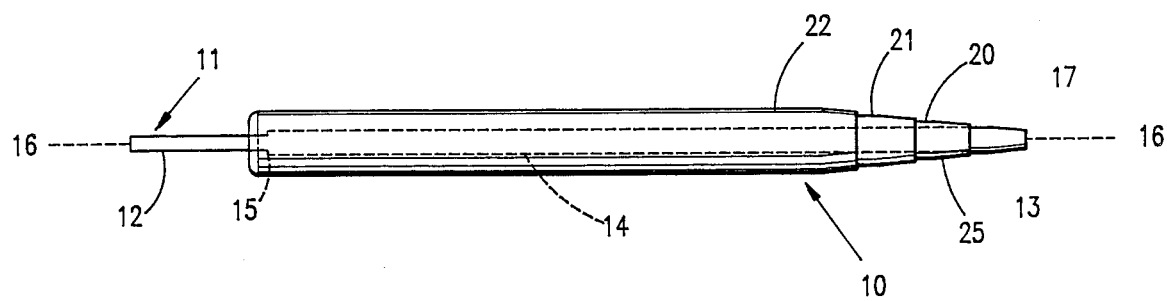
FIG. 1 shows a side, plan view of an assembled sequential dilation device in accordance with the present invention, with an enlarged cross-sectional view of its rearward end along a central axis.
Figure 3:
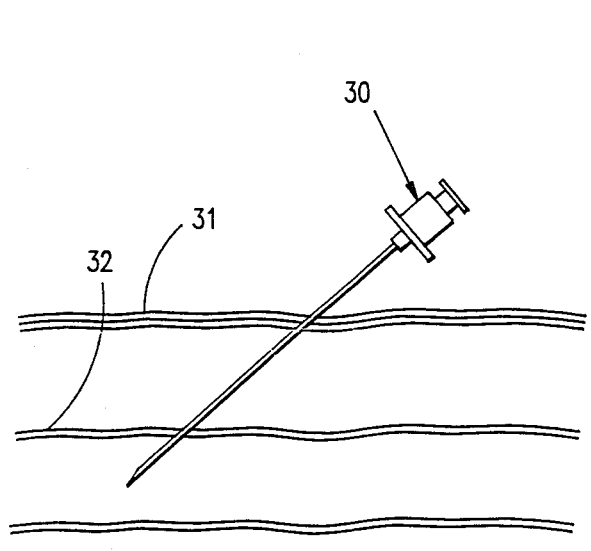
FIG. 3 graphically illustrates accessing a vessel by means of a needle.
Figure 4:
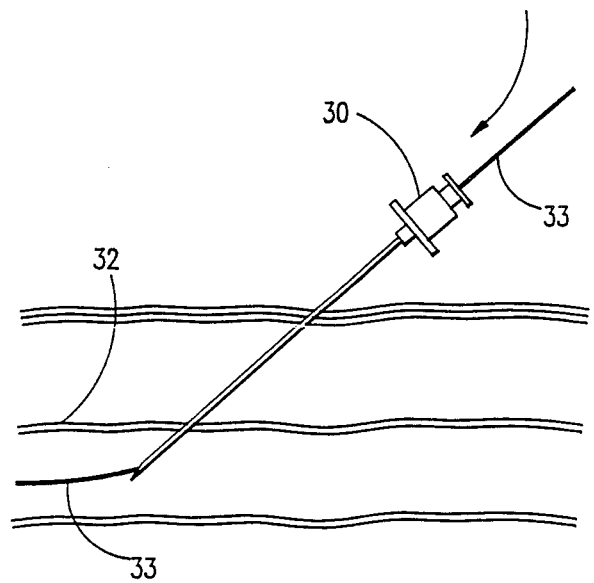
FIG. 4 illustrates the insertion of a guide wire through the lumen of the needle and into the vessel.

Referring now to the drawings:

A device for enabling the sequential dilation of a tissue opening is generally shown as item 10 in FIG. 1. This device comprises a first, elongated dilator element 11 which includes a tail section 12, a forward end 13 and an intermediate body 14 (shown in phantom line). The first dilator element 11 also includes rearwardly disposed shoulder structure 15 which is more clearly illustrated in the enlarged view of FIG. 1. The shoulder structure 15 is formed at the juncture of the tail 12 and intermediate body 14. This shoulder structure comprises a substantially planar, annular face at the end of the intermediate body 14, with the face being oriented in radial position with respect to the central axis 16. This annular face extends outward from the smaller diameter of the tail section 12 The function of this shoulder structure will become apparent from the following disclosure.

With respect to the configuration of the forward end 13, it should be noted that a gradual taper is formed at the distal section 17 to facilitate dilation at the percutaneous access point. This tapered structure extends from its small radius at the most forward point to a larger radius of uniform size extending along the intermediate body 14. The structure then is reduced to a smaller radius at the tail section 12 which extends from the shoulder structure 15 previously described.

Figure 5:
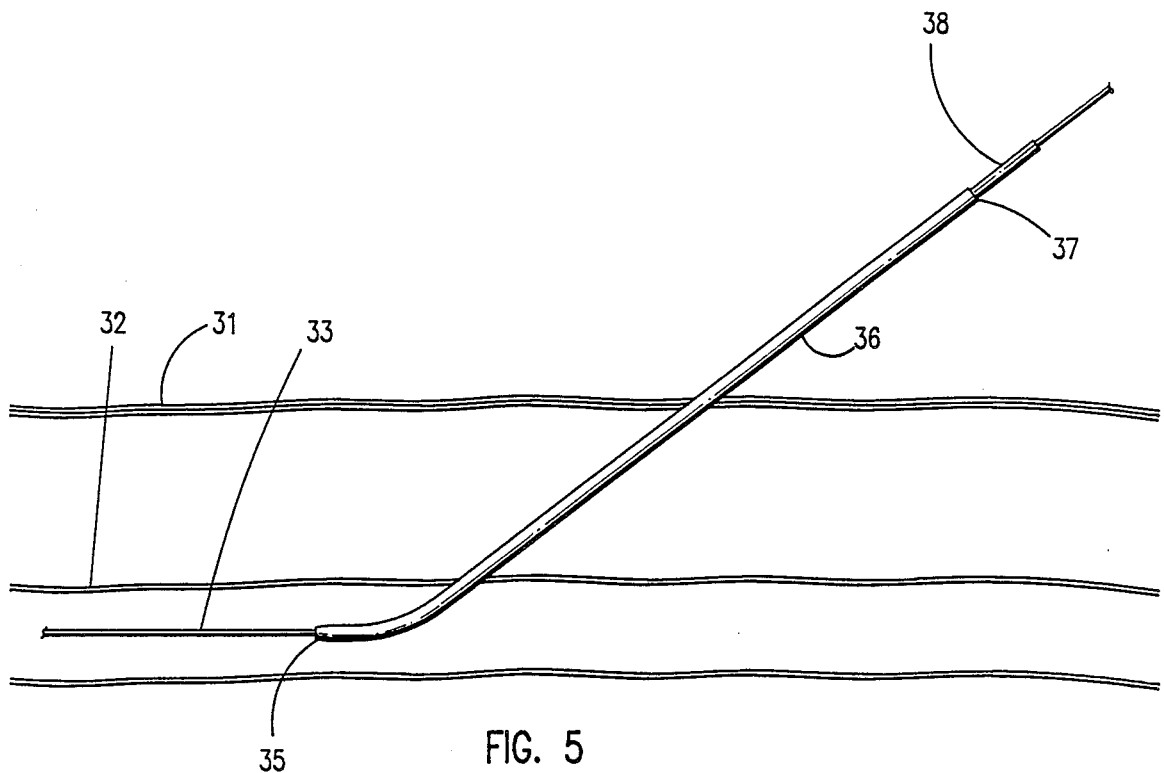
FIG. 5 depicts the emplacement of a first dilator element over the guide wire and into the vessel area.
Figure 6:
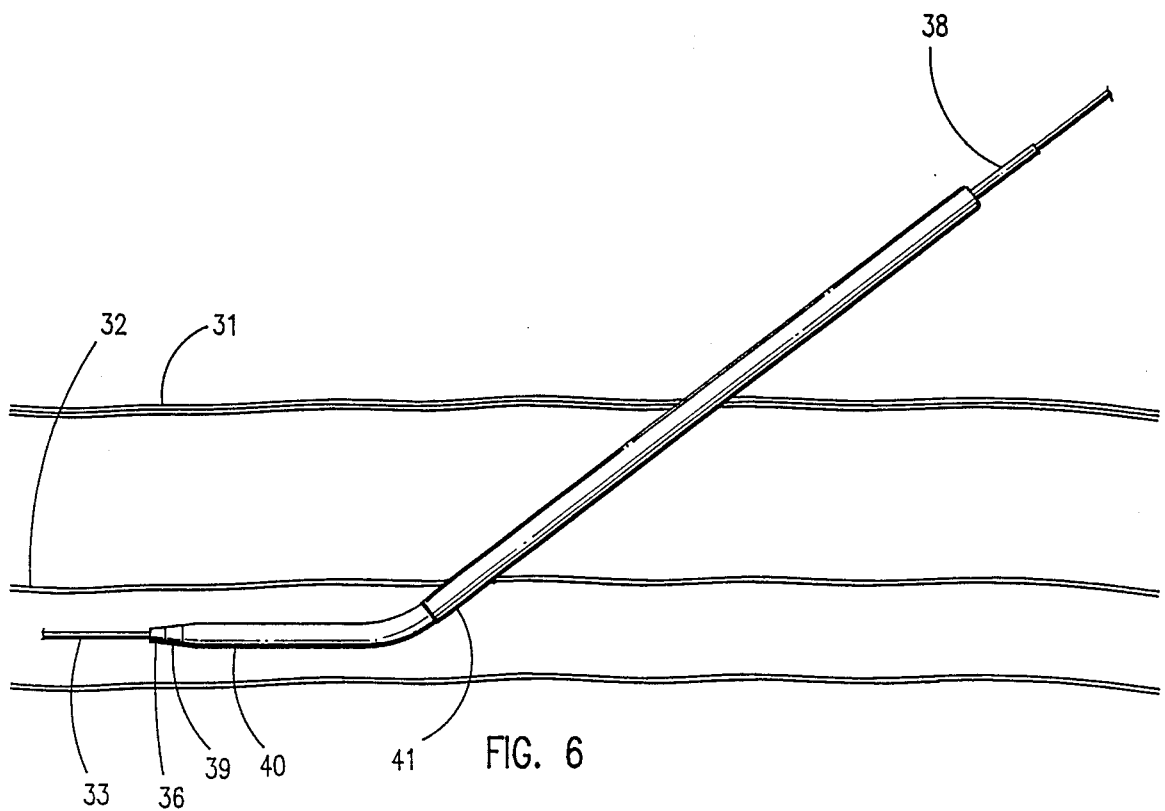
FIG. 6 graphically illustrates the sequential insertion of additional dilators over the first dilator element and into a forward most position within the vessel.
Figure 7:
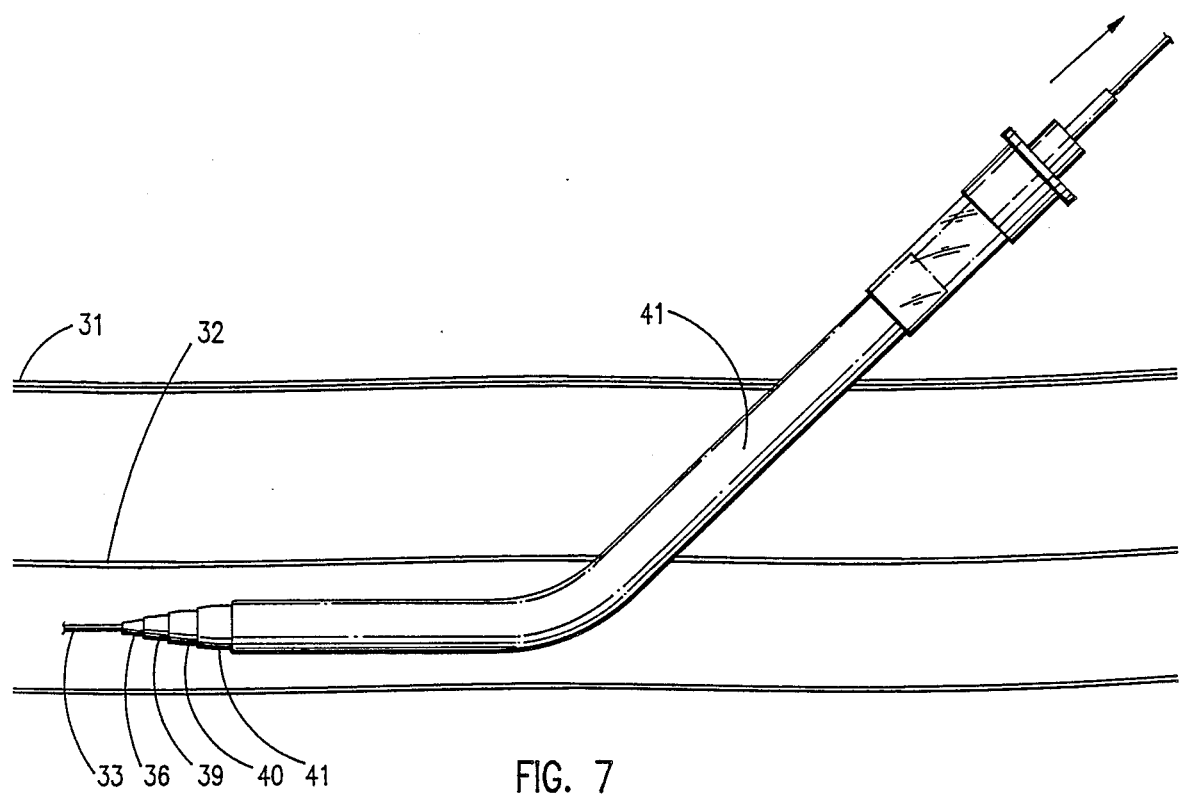
FIG. 7 illustrates the insertion of a sheath around the dilator device.

In its preferred embodiment, the first dilator element includes a central passage disposed along the full length thereof to facilitate insertion of a guide wire as shown in FIGS. 5–7. This procedure is discussed hereafter. Although the guide wire may not be essential, it provides a quick and easy method for inserting the first dilator element into its proper position within a vessel.

The first dilator element provides core support and operates as a mounting base for additional elongated, tubular dilators which are telescopically positioned around the first element 11. In FIG. 1, three additional tubular dilators 20, 21 and 22 are illustrated. Each additional tubular dilator has a tubular wall and a tubular opening which is slightly larger in inner diameter than the diameter of the first dilator element 11 or the additional tubular dilator 20 or 21 which comprises its telescopic mount.

For example, tubular dilator 20 is shown in a mounted position on the first dilator element 11. The tubular dilator 20 is structured with a tube wall of uniform diameter slightly larger than the outer diameter of the intermediate body 14. A forward section of this dilator 20 is tapered 25 from its outer diameter to its inner diameter. This taper enables gradual dilation of tissue from an opening size slightly larger than the intermediate body 14 of the first dilator element to the outer diameter of the tubular dilator 20. This outer diameter extends along the full length of the tubular dilator 20 to the rearward section shown in the enlarged view of FIG. 1.

Figure 2:
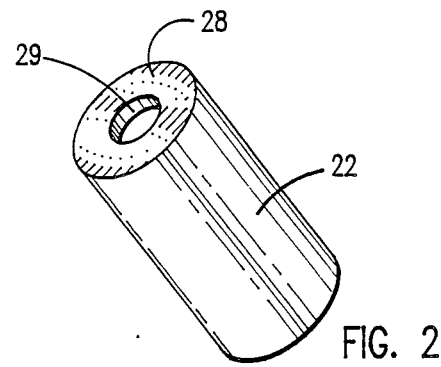
FIG. 2 shows a perspective end view of the outer dilator tube isolated from the remaining elements of the device.

The illustrated section in this enlarged view comprises the rearward end of the additional dilators, and also includes respective rearward blocking means 26, 27 and 28. This rearward blocking means is formed as an annular flange projecting radially inward from the tube wall of each dilator. For example, FIG. 2 illustrates the external-most dilator 22 which is telescopically mounted over dilator 21. Dilator 21 is, in turn, telescopically mounted over dilator 20, with each larger dilator being shorter in length than that dilator upon which it is mounted. Item 28 in FIG. 2 comprises the annular flange which serves as the blocking means and is adapted to provide limitation as to forward movement of the mounted dilators with respect to the first dilator element.

Each dilator also includes a rear opening 29 which permits passage of the tail section 12. The tail section (and enclosed guide wire) operate as a track for movement of each successive dilator into position. Except for this opening, the rear blocking member 26, 27 and 28 closes off an outer portion of the tubular opening and serves to abut against the enclosed tubular structure or shoulder structure of internal dilators.

Based on this description, it is clear that the primary operating element of the present structure is the first dilator element 11 which forms the mounting base for the additional dilators 20, 21 and 22. Each additional tubular dilator 20, 21 and 22 is of successively larger diameter, each having a slightly larger inner diameter than the outer diameter of the preceding dilator element. By providing such close-fitting construction, telescopic mounting of these components into a single sequential dilator device reduces blood loss and facilitates atraumatic entry through the skin and into the circulatory system.

Proper positioning of each successive dilator is ensured by the blocking structure previously described. Specifically, the first dilator element 11 is inserted into its desired location utilizing a guide wire which passes along an opening at the central axis 16. With the first dilator element in position, additional dilator 20 is positioned over the tail section 12 and guided onto the intermediate body 14 of the first element. When the blocking means 26 of dilator 20 butts against the shoulder section 15 of the dilator element, forward movement is limited. The second dilator 21 is then inserted in a similar manner, with the blocking means 27 contacting the tubular body of dilator 20, thereby restraining its forward movement. Dilator 22 is similarly limited by contact at the rearward end of dilator 21. Accordingly, a specific, seated configuration of the respective dilator elements is easily identified by the physician and ensures proper positioning during the cannulation procedure. By having a tail section 12 which extends well beyond the rearward end of the assembled dilators, the user may grasp hold and pull the whole assembly rearward. This will become more clear in the following procedural description.

FIGS. 3-9 graphically illustrate various steps in a cannulation procedure such as might be applied as part of a femoral bypass cannulation. The object of this procedure is to develop a percutaneous opening of at least 20 French outside diameter to enable insertion of a large catheter capable of blood transflow in high capacity. The procedure starts with entry of an 18 gage introducer needle 30 through the patient's skin 31 and into the interior of a vessel 32. A guide wire 33 of approximately 0.04 inch outer diameter is fed through the lumen of the needle and into the vessel 32.

With the guide wire 33 in place, the introducer needle 30 is removed. This guide wire will now operate as a positioning device for use with the subject invention.

The first dilator element corresponding to item 11 in FIG. 1 is inserted around the guide wire 33 through the central opening previously described. Again, this first dilator includes a forward end 35, an intermediate body 36, a shoulder section 37 and a removal tail 38 (corresponding to the tail section of FIG. 1). With this first dilator in place, the present system gives the advantage that sequential dilators of larger diameters can be placed into the vessel 32, dilating both the vessel walls and the subcutaneous and facia tisues 31, without the removal of any prior placed dilators. The tail 38 enables a user to retain a firm hold during insertion of additional dilators over the first dilator element and to maintain the device in a fixed, relative, percutaneous position.

FIG. 6 illustrates the positioning of additional dilators 39, 40 and 41 (corresponding to dilators 20, 21 and 22 in FIG. 1). The method of insertion has been previously described, including the final seated position wherein all four dilator elements are advanced to their final, forward position.

Figure 8:
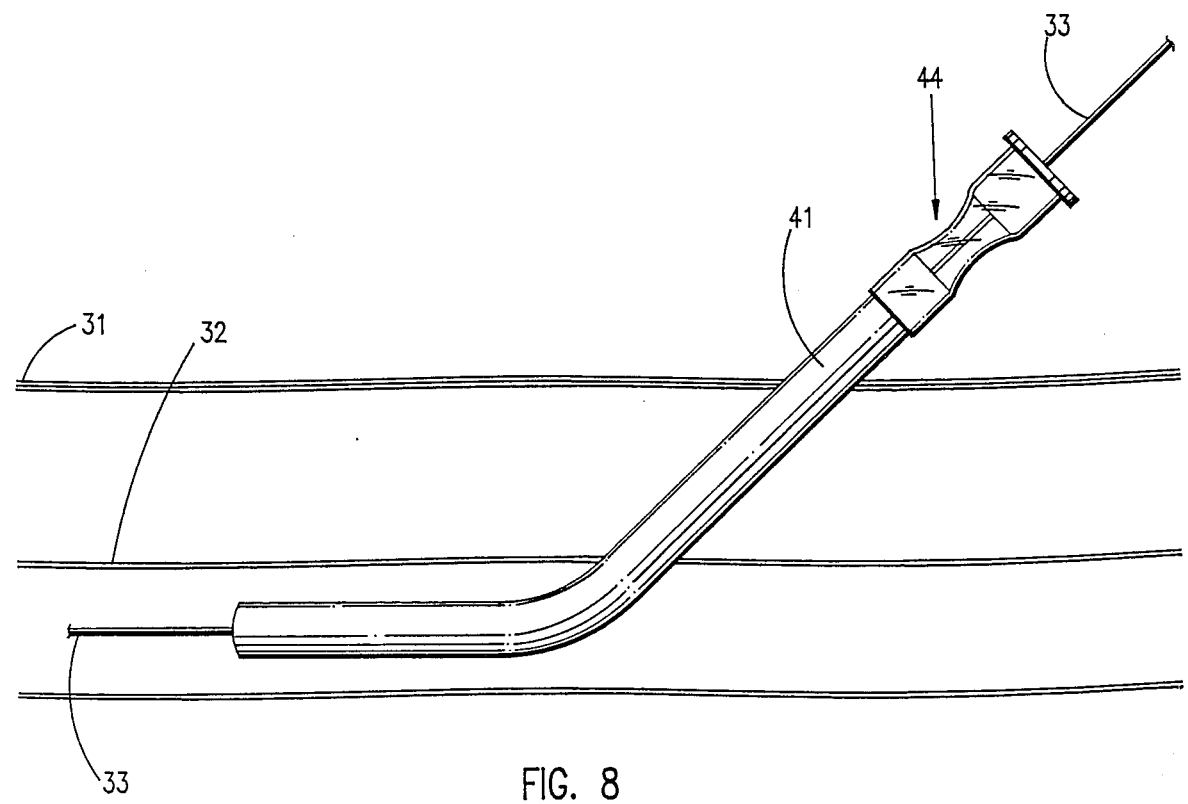
FIG. 8 illustrates the sheath in place with the dilator device removed.
Figure 9:
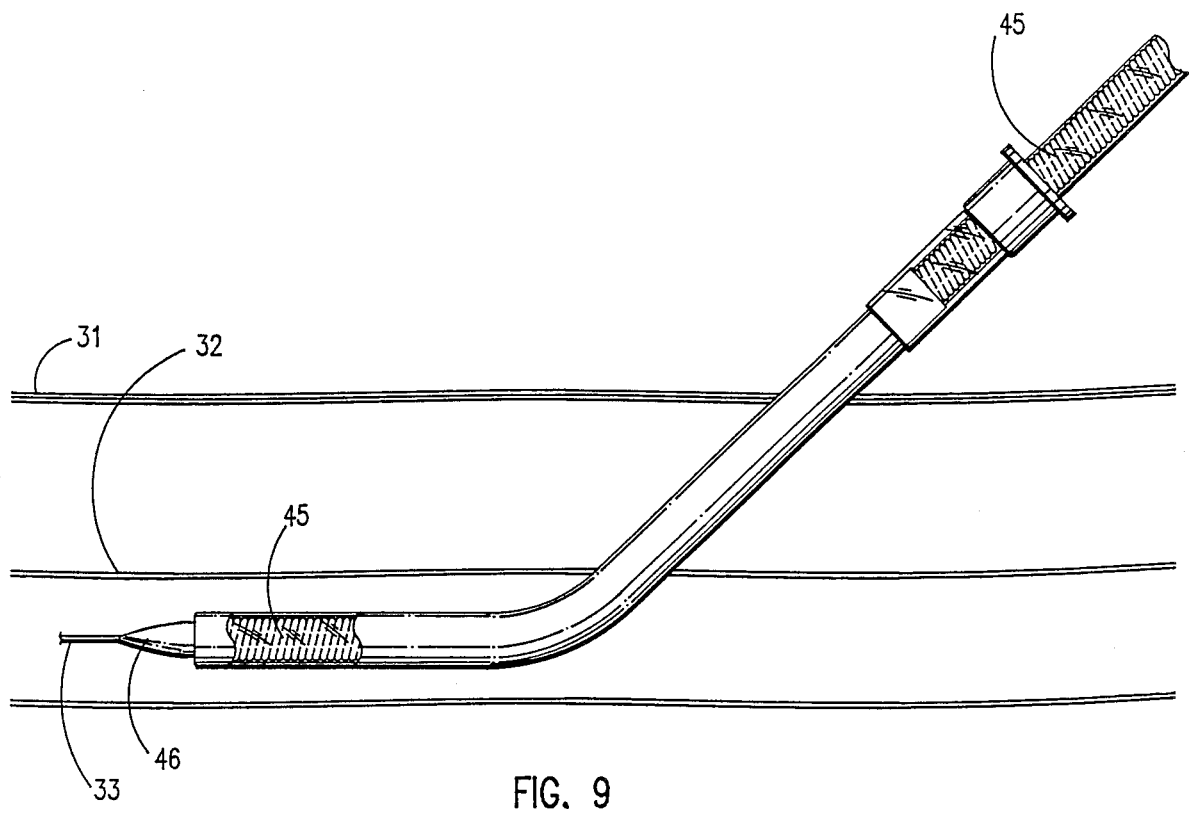
FIG. 9 graphically depicts the insertion of a cannula through the sheath.

FIG. 7 shows how the assembly would appear from an internal view with a sheath 42 positioned around the subject device After completion of the dilation procedure and sheath placement, the removal tail is grasped and pulled to remove all dilators simultaneously while leaving the guide wire and sheath in place as is shown in FIG. 8. Fingertip pressure is then used 44 to squeeze the PVC tubing length of the sheath and close the blood path. An arterial cannula is placed over the guide wire and inserted through the sheath and into the vessel until the proximal end of the cannula is secured into the hub of the sheath, as shown in FIG. 9. The obturator 46 is then removed and the proximal end of the cannula cross-clamped to prevent blood loss. This cannula is then secured in place and connected to the extracorporeal circuit for blood flow.

This procedure is applicable for a variety of applications with differing sizes of dilators. As an example, the outer diameter of the first element 11 in FIG. 1 may be approximately equal to 8 French, with each successive larger dilator having an increase of 4 French in diameter. Accordingly, dilator 20 would be at 12 French, 21 at 16 French and 22 at 20 French. By equalizing the intervals of increase in diameter sizes, a continuous rate of dilation is facilitated. For larger cannulation procedures, additional 24 and 28 French dilators may be added. Similarly, the lengths of dilators can vary with the following examples being provided:

8 French o.d. 32.5 centimeters
12 French o.d. 30.0 centimeters
16 French o.d. 27.5 centimeters
20 French o.d. 25.0 centimeters
20 French i.d. 20.0 centimeters Such a system would be compatible with a 20 French o.d. femoral venous drainage cannula at a length of 60 centimeters.

It will be apparent to those skilled in the art that the foregoing description is merely an example of the inventive concepts, and it is not to be construed as limiting. For example, removal by the tail section 11 could similarly be accomplished by utilizing a soft polymer or flexible material which is capable of being compressed within the rearward end of each additional dilator. The user could then pinch the rearward end of the device and capture the internal telescoping dilators in combination with the first dilator element. The device could then be removed in a similar manner as with the removal tail. Such construction is consistent with the numerous forms of biocompatible compositions currently being used for cannulation procedures.

The present invention fulfills a long recognized need in the medical field for a cannulation system which is adapted for femoral-to-femoral cardio-pulmonary bypass in a percutaneous fashion. Because no surgery is required, substantial savings are accomplished by utilization of other medical personnel who are not surgically specialized. The potential use for the present invention becomes even more significant in view of recent progress in percutaneous transluminal coronary angioplasty (PTCA) as a viable alternative to open-heart surgery. This new field depends on a viable method of percutaneous femoral cannulation which provides a high blood flow support system.

Emplacement of the present invention can be accomplished in less than 10 minutes, an improvement of almost 300 percent over the dominant prior art procedures. In addition, the present invention reduces post-surgical scarring and damage to the vessel walls, benefiting both the surgeon and patient. Because of its greatly simplified procedures, utilization of the subject sequential dilation device makes extracorporeal heart support a greatly simplified procedure which can now be adapted easily for bedside care. Because of the absence of surgical cut-down, the procedures can be implemented by a more extensive portion of the medical community, rather than merely cardiovascular surgeons.

I claim:

1. A device for enabling sequential dilation of a tissue opening to successively larger opening sizes, said device comprising:

a first elongated dilator element having a forward end, an intermediate dilator body of uniform diameter and a tail section of smaller diameter, the intermediate body including rearwardly disposed shoulder structure where the intermediate body joins the smaller diameter of the tail section; and at least one additional elongated, tubular dilator having a tubular wall and a tubular opening slightly larger in inner diameter than the diameter of the first dilator element and having a forward end, intermediate body, rearward end and rearward blocking means, said tubular dilator permitting telescopic mounting thereof around the first dilator element and movement to an extreme forward position limited by contact of the second element blocking means against the shoulder structure of the first element.

2. A dilation device as defined in claim 1, wherein the tail section has sufficient length to extend beyond the rearward end of the mounted second element to enable the user to grasp the tail section and pull the first and second elements rearward.

3. A dilation device as defined in claim 1, further comprising additional elongated, tubular dilator elements of successively larger diameter, each have a slightly larger inner diameter than the outer diameter of the preceding dilator element for enabling telescopic mounting thereof and each having rearward blocking means configured to limit forward movement of an outer dilator element by blocking contact between a rearward end of a preceding inserted dilator element and the blocking member of the outer element.

4. A dilation device as defined in claim 1, wherein the first dilator element includes a central passage disposed along the full length of the element to facilitate insertion of a guide wire therethrough.

5. A dilation device as defined in claim 3, wherein the first dilator element has an approximate outside diameter equal to 8 French and wherein a subsequent dilator element has an outer diameter of at least 20 French, intermediate dilator being sized with outer diameters at substantially equal diameter intervals between the extreme ranges of 8 and at least 20 French.

6. A dilation device as defined in claim 5, wherein each successive increase in outer diameter of the dilator elements is approximately equal to 4 French.

7. A dilation device as defined in claim 5, wherein a subsequent dilator element has an outer diameter of at least 28 French.

8. A dilator device as defined in claim 1, wherein the shoulder structure of the intermediate body comprises a substantially planar, annular face at the end thereof and oriented in radial position with respect to the central axis of the intermediate body.

9. A dilator device as defined in claim 1, wherein the rearward blocking means of the additional tubular dilator comprises an annular flange projecting radially inward from the tubular wall and closing off an outer portion of the tubular opening, being thereby adapted to contact the shoulder structure of the first dilator element to provide limitation as to forward movement of the additional dilator with respect to the first dilator element.

10. A dilator device as defined in claim 1, wherein the rearward end of the additional dilator comprises a flexible material capable of being compressed in response to an applied radial force to capture internal telescoping dilator in combination with the first dilator element to enable removal from a percutaneous implacement position.

* * * * *